(12) United States Patent
Hsieh

(10) Patent No.: US 9,610,255 B2
(45) Date of Patent: *Apr. 4, 2017

(54) LYCOPENE AND RESVERATROL DIETARY SUPPLEMENT

(71) Applicant: HSIEHS BIOTECH (SINGAPORE) PTE LTD, Singapore (SG)

(72) Inventor: Kun Lung Hsieh, Ho Chi Minh (VN)

(73) Assignee: HSIEHS BIOTECH (SINGAPORE) PTE LTD, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,245

(22) Filed: Nov. 7, 2014

(65) Prior Publication Data

US 2015/0132373 A1 May 14, 2015

Related U.S. Application Data

(63) Continuation of application No. 13/320,507, filed as application No. PCT/SG2009/000300 on Aug. 27, 2009, now abandoned.

(30) Foreign Application Priority Data

May 14, 2009 (SG) ................. 2009033010

(51) Int. Cl.
| | |
|---|---|
| A61K 31/05 | (2006.01) |
| A61K 31/01 | (2006.01) |
| A61K 45/06 | (2006.01) |
| A61K 9/20 | (2006.01) |
| A61K 9/48 | (2006.01) |
| A23L 33/105 | (2016.01) |

(52) U.S. Cl.
CPC ............ *A61K 31/05* (2013.01); *A23L 33/105* (2016.08); *A61K 9/20* (2013.01); *A61K 9/48* (2013.01); *A61K 31/01* (2013.01); *A61K 45/06* (2013.01)

(58) Field of Classification Search
CPC .. A61K 2300/00; A61K 31/375; A61K 31/01; A61K 31/355; A61K 31/385; A61K 31/015; A61K 31/05; A61K 31/065; A61K 31/122; A61K 31/185; A61K 31/195; A61K 31/198; A61K 31/35; A61K 31/404

See application file for complete search history.

(56) References Cited

U.S. PATENT DOCUMENTS

| | | |
|---|---|---|
| 2002/0182196 A1 | 12/2002 | McCleary |
| 2006/0003027 A1 | 1/2006 | Zhou |
| 2006/0014773 A1 | 1/2006 | McCleary |
| 2006/0020046 A1* | 1/2006 | Goralczyk ............ A23L 1/3002 514/763 |
| 2008/0248129 A1* | 10/2008 | Bartunek ............... A61K 31/01 424/630 |

FOREIGN PATENT DOCUMENTS

| | | | |
|---|---|---|---|
| JP | 2005526719 A | 9/2005 | |
| WO | WO2004/000043 A2 * | 12/2003 | ............... A23L 1/30 |
| WO | 2007131767 A2 | 11/2007 | |
| WO | 2008006581 A2 | 1/2008 | |
| WO | 2010082205 A1 | 7/2010 | |

OTHER PUBLICATIONS

Naviglio et al. ("Characterization of High Purity Lycopene from Tomato Wastes Using a New Pressurized Extraction Approach", J. Agric. Food Chem. 2008, 56, 6227-6231).*
Cheng et al. ("Structure-activity relationship studies of resveratrol and its analogues by the reaction kinetics of low density lipoprotein peroxidation", Bioorganic Chemistry 34 (2006) 142-157).*
Wu et al. ("Preparation, physiochemical characterization, and antioxidant effects of quercetin nanoparticles", International Journal of Pharmaceutics, 346 (2008) 160-168).*
CN Examiner, Office Action for CN 20090159426.9 Issued Nov. 5, 2012.
Sigma-Aldrich, "Dietary Antioxidants" Biofiles—Nutrition Research 2007, v 2, n 2, p. 10.
TW Examiner, Office Action for TW 098127219 Issued Sep. 18, 2013.
Amin et al., "Perspectives for Cancer Prevention with Natural Compounds", Journal of Clinical Oncology, Jun. 1, 2009, v 27 n 16, p. 2712-2725.
Merckling-Ruiz, Extended European Search Report for EP 09844719.6 Issued May 2, 2013.
JP Examiner, Office Action for JP 2012-510780 Issued Feb. 12, 2014.
Taylor, International search Report for PCT/SG2009/000300 Issued Oct. 13, 2009.
Sigma Chemical Company, Handbook/Catalogue, 1990, Product No. L9879 ( CAS Registry No. 502-65-8) p. 668.
Sigma Chemical Company, Biochemical & Reagents for Life Sciences Research Handbook/Catalogue, 2002-2003, Product No. R5010 (CAS Registry No. 501-36-0) p. 1803.
KU, Office Action for Korean Patent Application 10-2011-7028386 Issued Jan. 28, 2016.

* cited by examiner

*Primary Examiner* — Audrea Buckley
(74) *Attorney, Agent, or Firm* — Greer, Burns & Crain, Ltd.; Gregory P. Einhorn

(57) ABSTRACT

A dietary supplement is disclosed comprising lycopene and resveratrol in a range of ratio of lycopene:resveratrol from 1:10 to 10:1. Preferably, the ratio is 1:2 to 1:4. Lycopene is preferably of ≥95% purity and resveratrol is of ≥98% purity. Both lycopene and resveratrol may preferably comprise of nano-sized particles in crystal powder to optimize oral intake in the form of capsule or tablet. In small dosage, it should preferably include a minimum of 5 mg of lycopene and 10 mg of resveratrol. Various range of ratios of lycopene:resveratrol are provided for specific therapeutic purposes including 1:4 for symptomatic relief of arthritis, 1:2 for inhibiting melanoma or carcinoma malignancy, and 1:3 for inhibiting hyperlipoidemia. Generally, our dietary supplement composition may be used as an agent for anti-ageing, anti-oxidative, inhibiting cardiovascular diseases, relieving menopause symptoms and remission of post-operative cancer patients.

15 Claims, 3 Drawing Sheets

LYCOPENE AND RESVERATROL DIETARY SUPPLEMENT

CROSS-REFERENCE TO RELATED APPLICATIONS

This United States utility patent application a continuation of U.S. patent application Ser. No. 13/320,507, filed Jan. 30, 2012, now pending, which is the §371 national phase of PCT international patent application no PCT/SG2009/000300, having an international filing date of Aug. 27, 2009, which claims benefit of priority to Singapore Patent Application Serial Nos. SG 200903301-0, filed May 14, 2009. The aforementioned applications are expressly incorporated herein by reference in their entirety and for all purposes.

TECHNICAL FIELD

This invention generally relates to dietary supplement. It relates specifically to such dietary supplement compositions comprising lycopene and resveratrol exhibiting certain therapeutic effects, including anti-oxidant, anti-arthritis, suppressing carcinoma growth and mitigating hyperlipoidemia.

BACKGROUND ART

Lycopene, with a molecular formula of $C_{40}H_{56}$ and molecular weight of 536.85, has a molecular structure shown below.

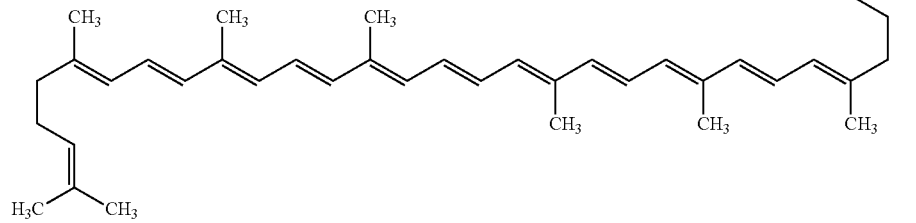

It is a carotenoid and the major target organs and tissues of lycopene in the human body are testis, prostate, liver and intestines. It is found to reduce incidence of prostatic carcinoma, metrocarcinoma, and pancreatic carcinoma more effectively than β-carotene (Giovannucci E., 1999, Gann P. H., 1999). As early as 1989, lycopene has been found to have the highest activity in quenching oxygen-singlet among all carotenoids including β-carotene (Di Mascio P.). The anti-oxidative activity of lycopene is found to be about 3.2-fold of that of β-carotene, and 100 times of that of vitamin E. Applied orally and absorbed through the intestinal tract, lycopene quenches free-radicals and thus protects tissues, cells, and DNA from oxidation by the free-radicals.

Previous studies have revealed a number of functions of lycopene: anti-ageing, enhancing immune health, reducing risk of cardiovascular diseases and incidence of malignancies, especially oral, throat, gastric, colon and uterus carcinomas. A meta-analysis carried out at Harvard University including 47,000 participants over a period of 6 years found that the incidence of prostatic carcinoma was over 30% lower in the lycopene group (Giovannucci, E., 1995). Furthermore, clinical trials revealed activity of lycopene in suppressing tumor growth and metastasis, especially effective for pancreatic, lung and gastric carcinomas (Giovannucci E., 1999; Gann R. H., 1999)

Because of its multiple beneficial effects, lycopene is now recognized as a star healthy food supplements in the 21st century and is gaining in popularity world-wide. Especially in developed countries including the U.S., Western Europe, Japan and Israel, huge wealth and efforts have been invested in related researches and in development of lycopene-containing drugs, food supplements, foods and cosmetics since 1990.

Resveratrol, with a molecular formula $C_{14}H_{12}O_3$ and a molecular weight of 228.25, is a terpenoid which is mainly contained in grape skin, peanut, pineapple and knotweed rhizome. This compound appears as an insipidity white crystal powder, slightly soluble in water but soluble in organic solvents such as ethanol and acetone. The structural formula of resveratrol is shown below.

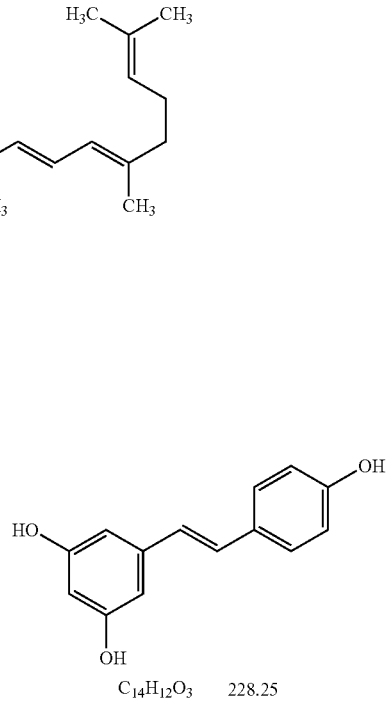

$C_{14}H_{12}O_3$     228.25

Resveratrol is known as an antioxidant, and has been found to decrease blood viscosity, suppress platelet-coagulation, enhance vasodilation and thus promote blood circulation. Because of its hypolipidemic feature, resveratrol plays an important role in preventing atherosclerosis and ischemic heart diseases. Resveratrol also has antineoplastic effect and is a natural substitute of estrogen. Further functionalities of resveratrol include anti-ageing effect, preventing oxidation of low-density lipoprotein (LDL) cholesterol, anti-inflammation and anti-allergic effect.

The main application of resveratrol is directed to acute infectious hepatitis, menostasis, rheumatism, bone and muscle pain, bronchitis, cholecystolithiasis, hypercholesterol and hypertriglyceride condition. The major target organs and tissues of resveratrol in human body are heart, blood vessels and skins.

There exist a number of patents either one of lycopene and resveratrol as the essential compound with optionally the other compound, or with both compounds in specific range of ratios which are claimed to be therapeutic for various ailments. New Zealand Patent No. 526350 (al-Shakarchi) disclosed lycopene in 0.1-2% w/v and resveratrol in 0.05-1.5% w/v in a preferred combination of a main complex composition which comprises metal salts, amino acids, amino alcohol and vitamin B complex. The lycopene: resveratrol disclosed is in the range of 1:15-40:1.

In U.S. patent publication No. 2008/0262081 (Raederstorff) lycopene with resveratrol is disclosed for anti-aging effect in form of a dietary supplement in wide-ranging ratios from about 1:1430-24:1. International patent publication No. WO 07131767 (DSM) discloses combination of lycopene and genistein for therapy of prostate carcinoma wherein in one of the embodiments resveratrol is preferably added such that lycopene: resveratrol range is about 1:2 to 1:3¾.

In International patent publication No. WO 2004/000043 (Perani) a food supplement is disclosed with both lycopene and resveratrol as antioxidants at 1:1 ratio. Another publication No. WO 2005/107729 (Kang) disclosed a skin disorder therapeutic composition comprising lycopene plus optionally resveratrol at a ratio of about 4:1.

Most commercially available preparations contain extracted lycopene as crystals which are water-insoluble and can not be efficiently absorbed in human intestinal tract. Natural lycopene is sourced from intracellular microsomes of plant cells and is similarly difficult to be absorbed directly by human body through oral intake, a problem not addressed by the prior art.

While the prior art also made wide therapeutic claims which have largely been speculative, our present invention endeavours to disclose certain combination ratios of lycopene to resveratrol for therapeutic use in specific ailments including arthritis, carcinoma generally and melanoma specifically, and in mitigating hyperlipoidemia.

SUMMARY OF DISCLOSURE

In the general embodiment of our invention, we disclose a dietary supplement composition comprising lycopene and resveratrol in a range of ratio of lycopene: resveratrol from 1:10 to 10:1. Preferably, the ratio is 1:2 to 1:4. In a first aspect of our composition, the lycopene is preferably of ≥95% purity and resveratrol is of ≥98% purity. Both lycopene and resveratrol may preferably comprise of nano-sized particles. Preferably, the particles are in the form of crystal powder to optimize intestinal absorption upon oral intake in the form of capsule or tablet. In small dosage, it should preferably include a minimum of 5 mg of lycopene and 10 mg of resveratrol.

In a second aspect of our composition, various range of ratios of lycopene: resveratrol are provided for specific therapeutic purposes including 1:4 for symptomatic relief of arthritis, 1:2 for inhibiting melanoma or carcinoma malignancy, and 1:3 for inhibiting hyperlipoidemia. Generally, our dietary supplement composition may be used as an agent for anti-ageing, anti-oxidative, inhibiting development of cardiovascular diseases, relieving menopause symptoms and remission of post-operative cancer patients.

LIST OF ACCOMPANYING DRAWINGS

The drawings accompanying this specification as listed below may provide a better understanding of our invention and its advantages when referred in conjunction with the detailed description the follows as exemplary and non-limiting embodiments of our composition, in which:

FIG. 1: is a column chart showing pain index of arthritis patients in placebo group, group treated with resveratrol only, group treated with lycopene only and group treated with combination of both resveratrol and lycopene;

DETAILED DESCRIPTION OF SPECIFIC EMBODIMENTS

Figure 1:
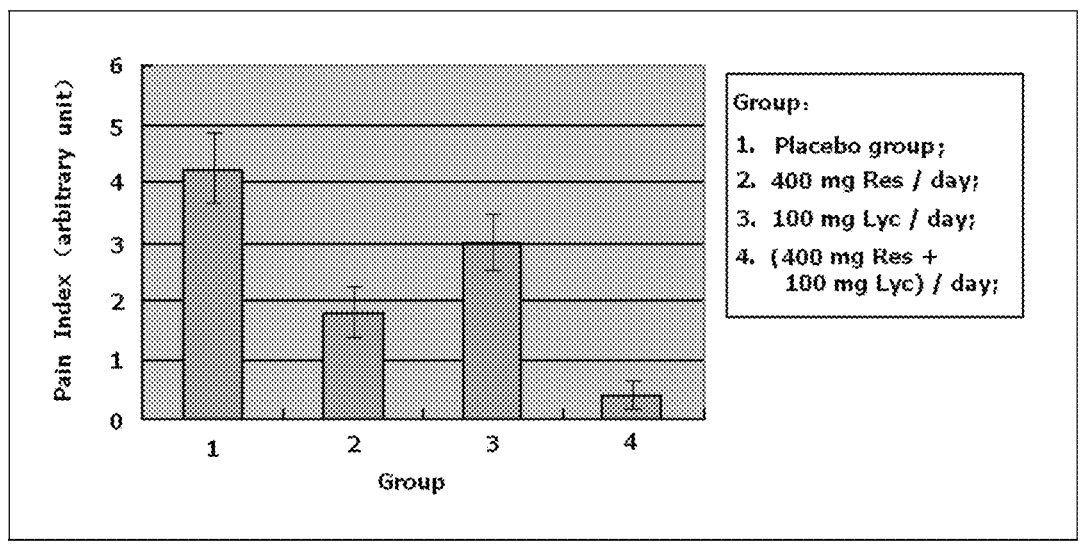

Our new composition is formulated based on the results of our research over years which revealed synergistic and complementary effects of the two potent anti-oxidative compounds, i.e. lycopene and resveratrol, as active ingredients. One main aspect of our findings concerns the bioavailability of these two compounds upon oral intake, and their respective distribution or deposition upon uptake in the human body.

After oral intake, over 90 percent of lycopene that is able to be adsorbed goes to the prostate and other internal organs while resveratrol is mainly distributed in the heart, circulation system, along respiratory tract and skin. From the following trials and results, it may be shown that the combination of the two compounds appears to show synergistic effects and to possess significantly higher activities in mitigating a number of diseases and malignancies and in improving conditions of some disorders than those of each of the compounds on its own.

In the broad, general embodiment of our dietary supplement composition, lycopene and resveratrol are to be admixed in a range of ratio of lycopene: resveratrol from 1:10 to 10:1 with the range of 1:2 to 1:4 considered as optimal ratio.

The bio-absorption of the two compounds following oral intake may be increased with the compounds provided in a certain high levels of purity and specific microscopic structural form. [By "microscopic" we mean particle size of a scale lower than micrometer, i.e. including nanometer and Å scale.]

Lycopene is preferably provided in purity ≥95% while resveratrol is preferably provided in purity ≥98%. Both compounds are also preferably provided in form of nano-sized particles, particularly micro-crystalline particles, or nano-crystals. These microscopic crystalline forms of lycopene and resveratrol may be produced with suitable conventional controlled recrystallization techniques such as single or multi-solvent solvent recrystallization, hot filtration recrystallization, and seeding, or a proprietary technology such as Elan Pharmaceutical's NanoCrystal™ technology for synthesizing nano-scale crystals optimized for water-solubility.

Examples of preparation of the composition comprising lycopene and resveratrol in various ratio are given in the following:

PREPARATION EXAMPLE 1

Lycopene: Resveratrol Composition in 1:2 Ratio 100 grams of lycopene with a purity of 95% and 200 g of resveratrol with a purity of 98% were mixed and sieved through a 100-mesh filter. The mixture was then capsulated, yielding a total of 1580 capsules with an average weight of 190 mg each.

PREPARATION EXAMPLE 2

Lycopene: Resveratrol Composition in 1:1 Ratio 200 g of lycopene with a purity of 95% and 200 g of resveratrol with a purity of 98% were mixed and sieved through a 100-mesh filter. The mixture was then capsulated, yielding a total of 2000 capsules, averaging 200 mg each.

PREPARATION EXAMPLE 3

Lycopene: Resveratrol Composition in 2:1 Ratio 200g of lycopene with a purity of 95% and 100g of resveratrol with a purity of 98% were mixed and sieved through a 100-mesh filter. The mixture was then capsulated, yielding a total of 1200 capsules, averaging 250 mg each.

For smaller dosages, our dietary supplement may be formulated as having, for example, 5 mg of lycopene and 10 mg of resveratrol in a 15 mg capsule or tablet. Conventional methods may be employed to make tablets such as the use of binding agent such as starch and/or magnesium stearate. For an example of lycopene: resveratrol composition in 1:3 ration 100 grams of lycopene with a purity of 95% and 300 g of resveratrol with a purity of 98% may be mixed with 40 g starch, and then mixed with 200 g starch slurry before tablet-making.

The second major aspect of our present invention concerns certain combination ratios of lycopene to resveratrol for therapeutic use in specific ailments including arthritis, carcinoma generally and melanoma specifically, and in mitigating hyperlipoidemia.

Trial 1-Symptomatic Relief of Arthritis

Forty subjects chosen for having a history of over 10 years suffering from knee joints pain. They were divided into 4 groups. Each group was served with placebo capsules, resveratrol (e.g. 400 mg/person/day) or lycopene (e.g. 100 mg/person/day), or the combination of both, respectively as indicated in FIG. 1. Five grades (as pain index) were designed for patients to define their painfulness.

Upon completion of the trial, they experienced complete relief or near complete relief from knee joint pain within one month. The best daily dose is speculated to be 100 mg of lycopene and 400 mg of resveratrol, i.e. lycopene: resveratrol in the ratio of 1:4 for efficacious symptomatic relief of arthritis. As is apparent from the bar chart of FIG. 1, the combination of resveratrol and lycopene showed synergistic effect on providing symptomatic relief of rheumatic knee joint pain.

Trial 2-Inhibition of Melanoma Malignancy

Figure 2:
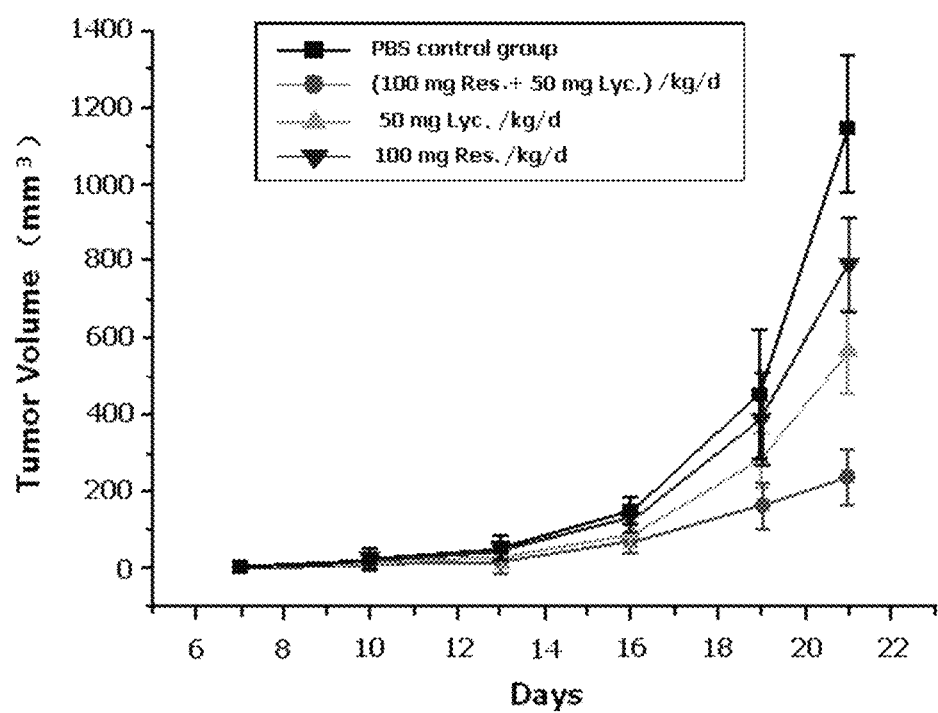
FIG. 2 is a line graph illustrating growth of melanoma graft in nude mice: untreated control, treated only with resveratrol, treated only with lycopene and combination of both resveratrol and lycopene.

Inhibition of melanoma growth is shown in FIG. 2 where the subjects are C57 mouse which are grafted with B16 murine melanoma tumour cells. From the line graph of FIG. 2, it is apparent that the combination of both lycopene and resveratrol has synergistic effect in suppressing growth of melanoma grafts. The optimal ratio of lycopene: resveratrol is suggested to be in the range of 1:2 for efficacious suppression of growth of carcinoma including melanoma.

In one specific case, a man with a tonsil tumor sized 3×3 cm, reported shrinkage of the tumor a size below the detectable range of magnetic resonance imaging after three-month intake of our dietary supplement comprising lycopene and resveratrol according to the aforesaid ratio. As is apparent from the bar chart of FIG. 2, the combination of resveratrol and lycopene showed synergistic effect in suppressing growth of tumor.

Trial 3-Lowering of Triglyceride Levels in Hyperlipoidemia

Figure 3:
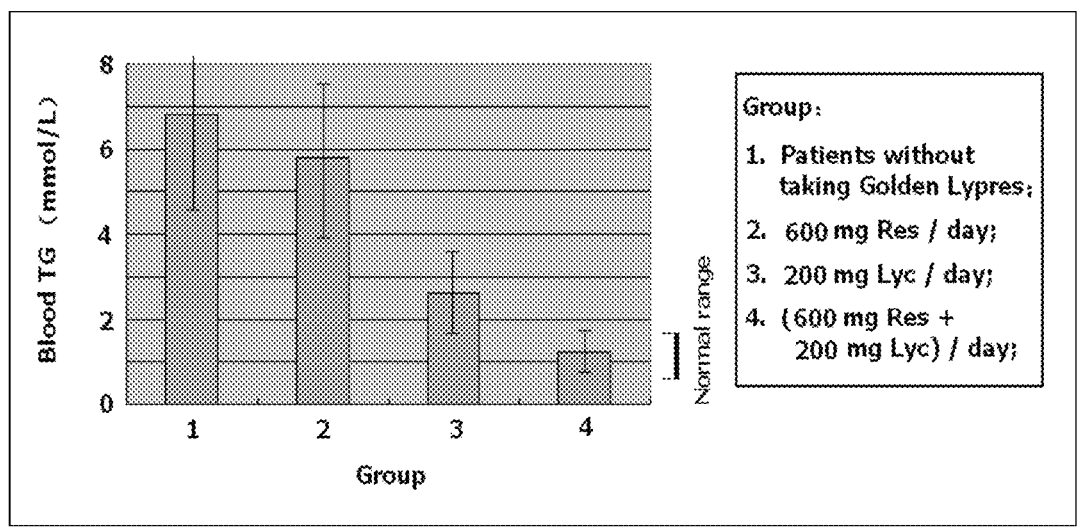
FIG. 3 is a column chart showing triglycerides levels in untreated control group, group treated with resveratrol only, group treated with lycopene only and group treated with combination of both resveratrol and lycopene.

Forty volunteer patients with hyperlipoidemia or having symptoms of high levels of triglyceride were enrolled in a one-month experiment. They were divided into 4 groups, and each group was given a different formulation of lycopene and/or resveratrol or none (control). The results are shown in FIG. 3. The group taking 600 mg resveratrol plus 200 mg lycopene achieved complete relief of hyperlipoidemia. Accordingly, the composition of these 2 phytochemicals in the ratio of lycopene: resveratrol at 1:3 may be considered optimal for inhibiting hyperlipoidemia. The combination of resveratrol and lycopene showed synergistic effect in lowering the level of triglycerides in blood.

Further health promoting effects of our preparation of lycopene and resveratrol may be expected to include anti-ageing, anti-oxidative, inhibiting cardiovascular diseases, relieving menopause symptoms and remission of post-operative cancer patients.

It would be apparent to a person skilled in the art that the suggested methods of obtaining the 2 active ingredients, i.e. lycopene and resveratrol, in their respective purity and nano-crystalline form may be obtained from alternative or modified techniques. The aforementioned ratios of lycopene and resveratrol are suggestive based on our trial results and the respective experimental conditions and may be subject to variance or tolerances. Many of the formulation or dosage techniques described above may also be similarly achieved with other conventional methods known to the notional skilled person. These modifications, adaptations and alternatives are to be considered as equivalents to our invention and fall within the scope and letter of the following claims.

LIST OF REFERENCES

Giovannucci, E. L., Ascherio, A., Rimm, E. B., Stampfer, M. J., Colditz, G. A., and Willett, W. C. *Intake of carotenoids and retinol in relationship to risk of prostate cancer*. J. Natl. Cancer Inst. 1995; 87: 1767-1776.

Giovannucci E. *Tomatoes, tomato-based products, lycopene, and cancer: Review of the epidemiologic literature*. Journal of the National Cancer Institute 1999; 91: 317-331.

Di Mascio P., Kaiser S., Sies H. *Lycopene as the most efficient biological carotenoid singlet oxygen quencher*. Arch Biochem Biophys. 1989; 274(2): 532-538.

Gann P H, Ma J, Giovannucci E, Willett W, Sacks F M, Hennekens C H, Stampfer M J. *Lower prostate cancer risk in men with elevated plasma lycopene levels: results of a prospective analysis*. Cancer Res. 1999 Mar. 15; 59(6):1225-30.

Edward Giovannucci, Eric B. Rimm, Yan Liu, Meir J. Stampfer, Walter C. Willett, *A Prospective Study of Tomato Products, Lycopene, and Prostate Cancer Risk*, J. Natl Cancer Inst. 2002 Mar. 6; 94(5):391-8.

What is claimed is:

1. A composition consisting of lycopene and resveratrol in a synergistic ratio, in a range of a weight ratio of lycopene:resveratrol from 1:2 to 1:4,
   wherein the lycopene has a purity of 95% or greater, and the resveratrol has a purity of 98% or greater, and
   wherein the composition is formulated as a dietary supplement composition.

2. The composition of claim 1, wherein the lycopene comprises nano-sized particles.

3. The composition of claim 1, wherein the lycopene comprises or is in the form of a crystal powder.

4. The composition of claim 1 wherein the resveratrol comprises nano-sized particles.

5. The composition of claim 1, wherein the resveratrol comprises or is in the form of a crystal powder.

6. The composition of claim 1, comprising lycopene:resveratrol in the weight ratio of 1:4, formulated for symptomatic relief of arthritis.

7. The composition of claim 1, comprising lycopene:resveratrol in the weight ratio of 1:2, formulated for inhibiting a carcinoma malignancy.

8. The composition of claim 7, formulated for inhibiting melanoma malignancy.

9. The composition of claim 1, comprising lycopene:resveratrol in the weight ratio of 1:3, formulated for inhibiting hyperlipoidemia.

10. The composition of claim 1, formulated for oral intake.

11. The composition of claim 1, formulated in a capsule or a tablet.

12. The composition of claim 1, comprising at least about 5 mg of lycopene and about 10 mg of resveratrol.

13. The composition of claim 1, formulated in a capsule or a tablet form and comprising a unit weight of a range of from between about 190 to 400 mg.

14. The composition of claim 1, formulated for use as an agent for anti-ageing, inhibiting development of cardiovascular diseases, relieving menopause symptoms, remission of post-operative cancer patients, or for use as an anti-oxidative.

15. The composition of claim 1, further comprising and formulated with a binding agent, optionally wherein the binding agent comprises a starch or a magnesium stearate.

* * * * *